United States Patent [19]

Dessi'

[11] Patent Number: 5,086,713
[45] Date of Patent: Feb. 11, 1992

[54] REFUSE-TREATING UNIT

[75] Inventor: Antonietta Dessi', Vaduz, Liechtenstein

[73] Assignee: Biogen Ltd., Liechtenstein

[21] Appl. No.: 605,572

[22] Filed: Oct. 29, 1990

[30] Foreign Application Priority Data

Nov. 1, 1989 [CH] Switzerland ............... 3954/89

[51] Int. Cl.$^5$ .................... F23G 5/00; F23G 5/10
[52] U.S. Cl. ..................... 110/250; 110/223; 110/242
[58] Field of Search ........... 110/223, 229, 233, 242, 110/250; 100/102, 229 A

[56] References Cited

U.S. PATENT DOCUMENTS 3,383,228  5/1968  Rekate et al. ............ 110/223 X
4,706,560  11/1987  Capodicasa ............... 100/102
4,897,222  1/1990  Muntzel et al. ........... 100/229 A X

FOREIGN PATENT DOCUMENTS 0241981  11/1985  Japan ..................... 110/223
1212400   8/1989  Japan ..................... 110/223

Primary Examiner—Edward G. Favors
Attorney, Agent, or Firm—Laff, Whitesel, Conte & Saret

[57] ABSTRACT

The described refuse-treating unit (1) comprises a treatment chamber (2) adapted to hold a predetermined amount of refuse (6), a sterilization apparatus acting on the treatment chamber and adapted to administer heat to the refuse amount (6) until said amount is at least partly converted to a sterilized mass in a pasty state, and a compacting device (7, 8, 9) adapted to press the refuse amount (6) at least partly in a pasty state together, and convert it to a compact block (10).

9 Claims, 2 Drawing Sheets

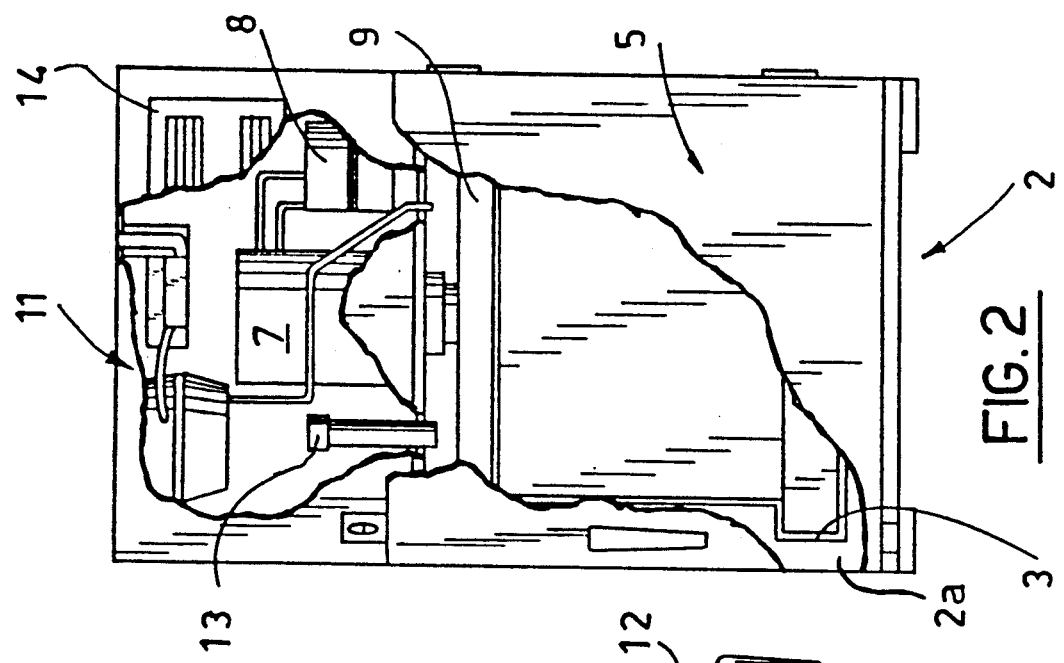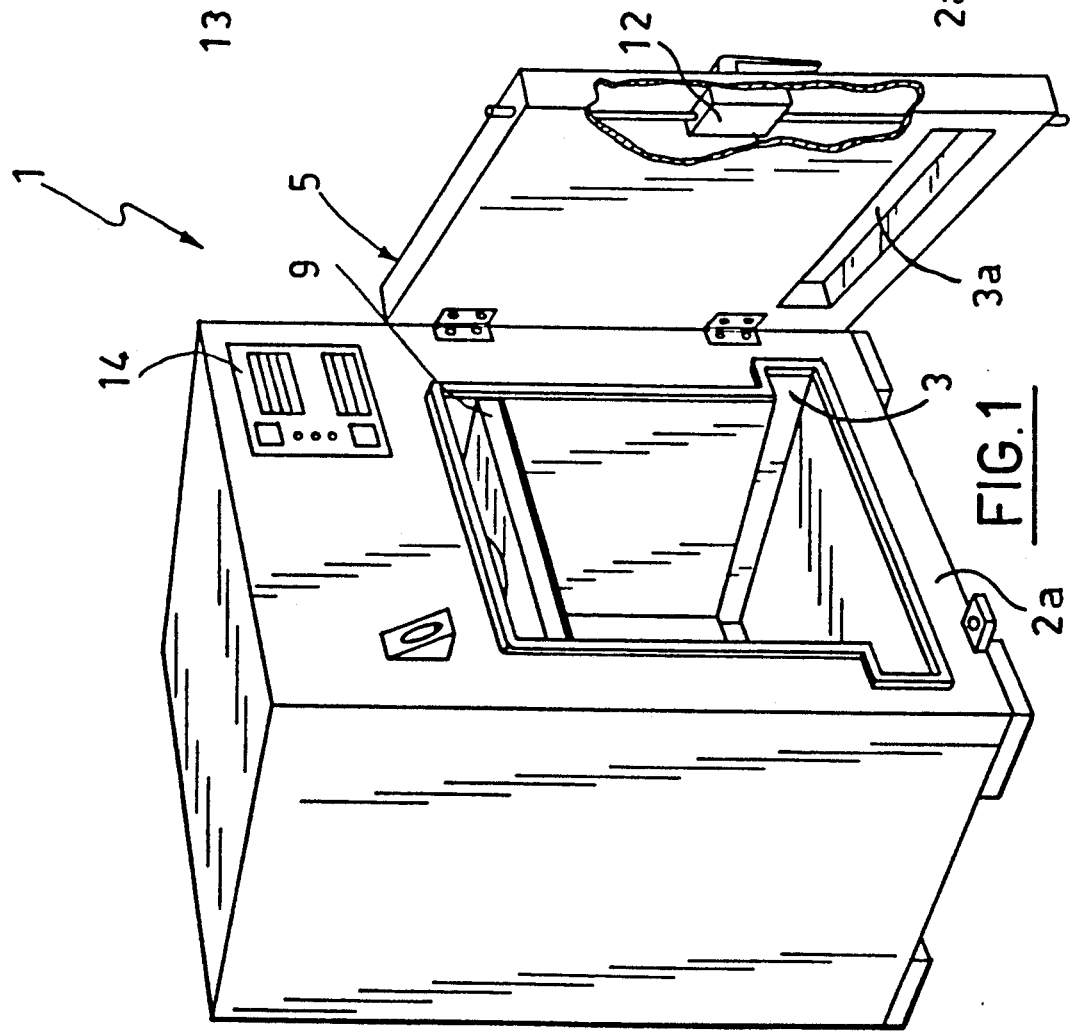

REFUSE-TREATING UNIT

BACKGROUND OF THE INVENTION

1. Field of the Invention

The present invention relates to a refuse-treating unit. The kind of refuse treated in accordance with the present invention may be hospital, industrial and municipal wastes.

2. Prior Art

It is known that presently the refuse collection, particularly in hospitals, first aid stations, medical laboratories and similar facilities is generally accomplished by the use of plastics bags or cardboard containers inside which plastics envelopes are arranged.

From studies carried out in Europe it appears that once said bags have been filled, they are partly conveyed to refuse dumps or incinerators where they are burnt, and partly collected by specialized firms or have an unknown destination. Due to the spreading of some types of infections and also to the psychosis related thereto above all in recent years, in hospitals there has been a tendency of absorbing all refuse in the particular category of special refuse for which the sterilization in suitable furnaces is provided before they are destined for disposal.

The disposal techniques applied to hospital refuse have however some limits and drawbacks.

The first drawback resides in the high costs necessary for the above operations, which cost is due both to the important volume of matter to be transported and to the fact of considering each hospital refuse as a special one.

A second drawback to be taken in still greater account than the former is represented by the lack of safety when wastes are transported at the inside and outside of the units where they are produced because the containers for example do not give the complete certitude that needles or infect biological products do not come out.

In addition, even during the sterilization operations, where they are carried out, some drawbacks may sometimes occur such as for example the container breakage inside the furnaces, which makes the removal of the sterilized refuse rather difficult.

Finally it is to be pointed out that the refuse incineration when plastic materials are contained in the refuse matter—said plastic materials being increasingly more used in hospitals and in the different medical units—involves the generation and the discharge to the surrounding atmosphere of harmful substances such as for example dioxine.

SUMMARY OF THE INVENTION

Under this situation, the technical task underlying the present invention is to devise a refuse pre-treating unit capable of substantially eliminating the above drawbacks.

Within the scope of this technical task it is an important object of the invention to devise a treating unit enabling the refuse collection and disposal costs to be drastically reduced.

Another important object of the invention is to provide a treating unit allowing the refuse to be transported in a completely safe and riskless manner.

A further object of the invention is to devise a treating unit not only enabling an easy sterilization of the refuse but also ensuring an easy recycling of the same, the recycled product being used above all in the building field, so that the disposal of said refuse also becomes advantageous from an economical point of view.

Yet another object of the invention is to provide a treating unit adapted to be easily installed in the locations where the refuse is produced and that does not give rise to the production of polluting substances.

A still further object of the invention is to provide an embodiment thereof which is advantageous in itself and at the same time representing a technical progress in the specific field.

The foregoing and further object that will become more apparent in the course of the following description are substantially attained by a refuse-treating unit comprising a treatment chamber adapted to contain a predetermined amount of said refuse, a sterilization apparatus acting on said treatment chamber and adapted to administer heat to said refuse amount as far as it is partly converted to a sterilized mass in a pasty state, and a compacting device adapted to press said refuse amount at least partly in the pasty state together, and convert it to a compact block.

Further features and advantages of the invention will best be understood from the description of a preferred embodiment of a refuse-treating unit, given hereinafter by way of non-limiting example with reference to the accompanying drawings, in which:

FIG. 1 is a perspective view of a treating unit in accordance with the invention;

FIG. 2 is a partly sectional view of the unit shown in FIG. 1;

Figure 7:
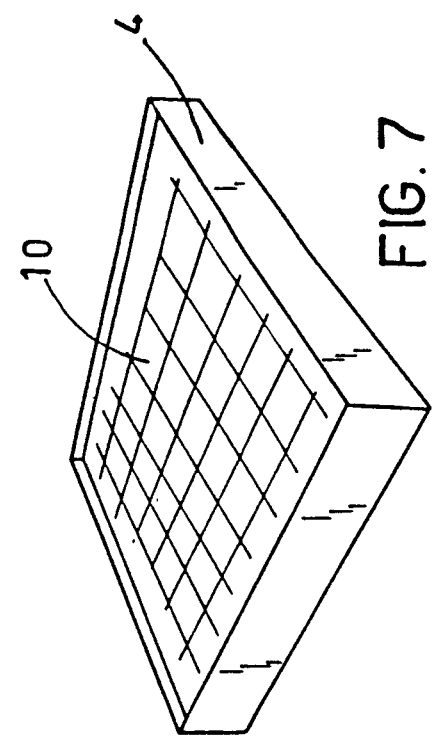
Figure 6:
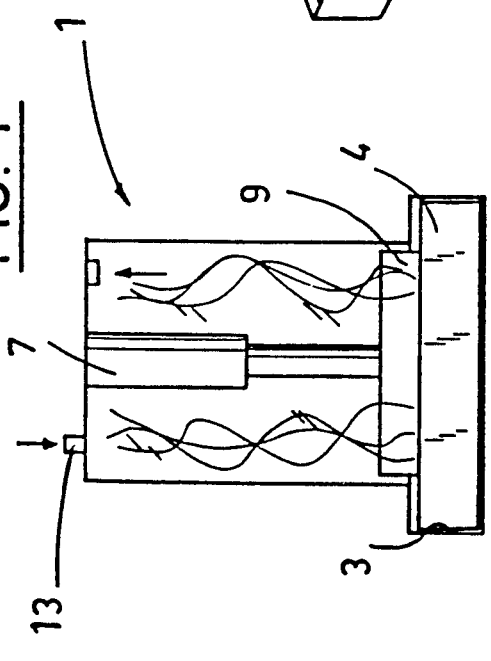

FIGS. 3, 4, 5 and 6 diagrammatically show the sequential steps of the operating cycle of the treating unit;

FIG. 7 is a perspective view of the product as it appears after each cycle.

Referring to the drawings, the refuse-treating unit for hospital wastes in accordance with the invention has been generally identified by reference numeral 1.

It comprises a treatment chamber 2 provided with perimetrical walls having internally-formed recessed housings 3, located close to a bottom wall 2a, said housings being designed to receive the peripheral edges of a holding tray 4 preferably of the disposable type, consisting for example of an aluminium basin of thin thickness.

The treatment chamber 2 also comprises a tight-closure access door 5 provided with a recessed housing 3a similar to the recessed housings 3 formed in the chamber walls. In this way the holding tray 4, when the access door 5 is closed, is housed in a reinforcement die completely surrounding its side edges. A refuse container or bag 6 can be put on said holding tray 4. The refuse matter generally consists of different kinds of needles and syringes, plasters, bandages, cotton-wool, stool-holding and urine-holding containers or bags, drains, test-tubes, gloves, tampons and any other kind of refuse produced in the hospital departments or first aid stations. Obviously it is also possible to use the treating unit of the invention for other kinds of refuse such as municipal refuse and industrial wastes, for example plastics bottles and containers.

Disposed within the walls of the treatment chamber is a sterilization apparatus consisting for example of resistors (not shown in the drawings) adapted to administer heat to the amount of refuse contained in the bag 6, until said amount is at least partly converted to a sterilized mass in a pasty state.

A compacting device defined for example by a pneumatic cylinder 7 operated by a compressor 8 is provided in the upper part of the treatment chamber 2. The pneumatic cylinder 7 has a work plate 9 adapted to act on said refuse amount at least partly in a pasty state, so as to convert it to a compact block or "briquette" 10. The work plate 9 has an extension corresponding to the surface of the holding tray 4 and is counteracted in its vertical downwardly-directed movement by the bottom wall 2a of the treatment chamber 2 on which said holding tray 4 rests.

Provision is also made for an apparatus 11 designed to remove and filter the air present in the treatment chamber 2 and mixed with gases produced during the unit 1 operation. In order to prevent unforeseen openings in operation, the access door 5 is comprised of a safety locking device 12. Also an inlet valve 13 adapted to let air flow into the treatment chamber 2 is provided.

Finally a control unit 14 carries out the automatic control of the sequentially programmed operations of said sterilization apparatus, compacting device 7, suction and filtering apparatus 11, inlet valve 13 and safety locking device 12.

OPERATION

Operation of the refuse-treating unit for hospital wastes according to the invention described above mainly as regards structure, is as follows.

After introducing the refuse bag 6 into the treatment chamber 2 on the bottom of which the holding tray 4 has been previously arranged and fitted into the recessed housings 3, the access door 5 is closed and the operating cycle is triggered by depressing an appropriate key. The closure of the access door 5 provided with the recessed housing 3a enables the tray 4 edges to be completely entrapped so that said tray can also withstand very high pressures.

Figure 3:
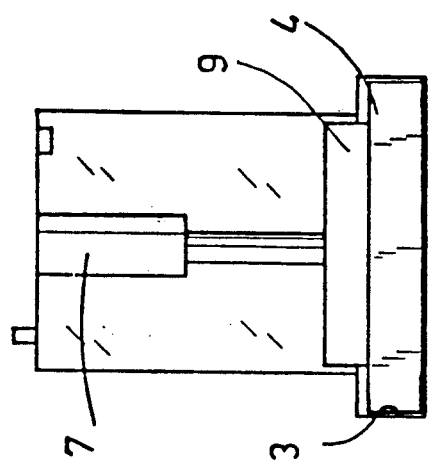
Figure 4:
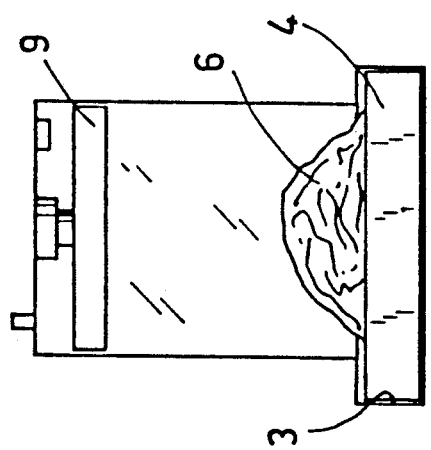
Figure 5:
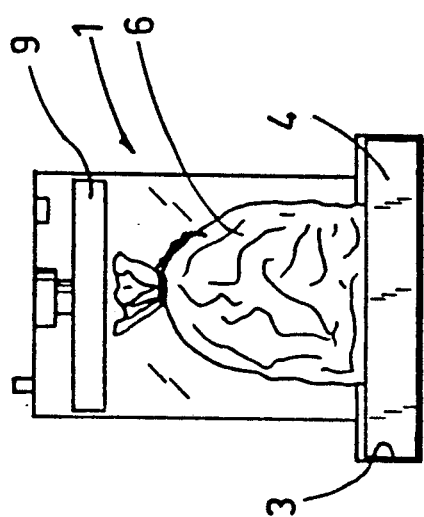

The sterilization apparatus brings the temperature of the refuse matter to values approximately on the order of 240° C. At the above temperature some refuse for example plastics wastes, melt or at all events reach the pasty state (FIG. 4). When the sterilization step is over, the pneumatic cylinder 7 sends the work plate 9 downwardly and said plate presses the refuse amount which has already reduced its volume and makes it more compact (FIG. 5) thereby forming the compact block 10 substantially in the form of a "briquette" that is completely contained within the tray 4 edges. The volume of the compact block can even be equal to about 10% of the starting volume of the container 6.

When the work plate 9 has moved upwardly, the suction and filtering apparatus 11 draws the air mixed with the produced bad-smelling gases out of the treatment chamber 2. This air is not polluted since in the treatment chamber 2 no incineration has occurred and at all events the air is filtered.

Then cooling air is introduced through the inlet valve 13 and finally the control unit 14 signals that the operating cycle is over. Only now the safety locking device 12 enables the opening of the access door 5 and therefore the compact block 10 can be withdrawn from the treatment chamber by moving the holding tray 4. The compact block or briquette 10 thus obtained therefore does not come into contact with the operator's hands although this is not a very important problem since the block is sterilized.

The blocks or briquettes obtained can be temporarily stored without any danger into appropriate cabinets waiting for being collected and subsequently utilised.

After workings carried out on the blocks 11, such as for example rolling, milling and painting processes, the same can be recycled and become ready for the most different fields of use.

By way of example only, the following possible uses are mentioned: garden tiles, roofing tiles, bricks, covers for floating wharves, since the blocks are imputrescible, wall insulation. In addition crushed compact blocks 11 or scraps resulting from their workings can be mixed with tar so as to form, for example, a road blanket which is adapted to absorb the expansions due to frost without damages, or they can be used for filling particular manufactured articles using an injection or extrusion system.

The invention attains the intended purposes and reaches important advantages.

In fact, even if a recycling of the compact blocks obtained as a final product is not provided, the treating unit in accordance with the invention enables a drastic reduction in the volume of the refuse so that, if the refuse blocks need to be subsequently disposed of in the traditional manner into incinerators, the transport costs will be greatly reduced.

It is also to be pointed out that the compact blocks thus obtained can be easily and safely moved, as they consist of sterilized material reduced to shapes adapted to be easily transported.

Finally if a reuse of the compact blocks thus obtained is foreseen, a further important saving can be made in the overall management of wastes, and it is also possible to contribute to a reduction of the atmospheric pollution.

It will be moreover recognized that the particular embodiment shown is also advantageous in its most specific aspects that are apparent from the specification and drawings.

The above described invention is susceptible of many modifications and variations, all of them falling within the scope of the invention idea. In addition all of the details can be replaced by technically equivalent elements. In carrying out the invention practically, the materials shapes and sizes can be of any nature and magnitude in accordance with requirements.

I claim:

1. A refuse-treating unit comprising:
   a treatment chamber containing a predetermined amount of refuse and having a tight-closure access door and a safety locking device which prevent said door from opening while said treating unit is in operation;
   a suction and filtering apparatus which removes and filters air and gases produced within said treatment chamber;
   an inlet air valve that admits cooling air in said treatment chamber;
   means forming a sterilization apparatus disposed within said treatment chamber and including resistors which heat said refuse amount until the refuse amount is reduced, at least partly, to a pasty state, and
   a compacting device having a fluid-operated cylinder which includes a work plate that presses and converts said refuse amount, which was previously heated to a pasty state, into a compact block.

2. The treating unit of claim 1 wherein said sterilization apparatus heats said refuse amount at approximately 240° C.

3. The treating unit as claimed in claim 1, wherein a holding tray is provided which is insertable into said treatment chamber and is adapted to form a bearing surface for said refuse amount and define an envelope partly surrounding said compact block.

4. The treating unit as claimed in claim 3, wherein said treatment chammber is comprised of perimetrical walls provided with recessed housings into which the peripheral edges of said holding tray can be inserted so as to partly form a reinforcement die for the tray itself.

5. The treating unit as claimed in claim 3, wherein said holding tray is of the disposable type and represents the displacement means for said compact block.

6. The treating unit as claimed in claim 3, wherein said work plate has an extension substantially corresponding to the surface of said holding tray.

7. The treating unit as claimed in claim 3, wherein said fluid-operated cylinder has a substantially vertical operating direction.

8. The treating unit as claimed in claim 3, wherein said holding tray rests on a bottom wall in said treatment chamber, said bottom wall defining a surface counteracting the action of said work plate during said vertical operation.

9. The treating unit as claimed in claim 1, wherein a control unit is provided which is adapted to automatically control the programmed operating sequence of said sterilization apparatus, compacting device, suction and filtering apparatus, inlet valve and safety locking device.

* * * * *